US00PP17267P2

(12) United States Plant Patent
Austin

(10) Patent No.: US PP17,267 P2
(45) Date of Patent: Dec. 12, 2006

(54) SHRUB ROSE PLANT NAMED 'AUSIMMON'

(50) Latin Name: *Rosa hybrida*
Varietal Denomination: AUSimmon

(75) Inventor: David C. H. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 1 day.

(21) Appl. No.: 11/048,360

(22) Filed: Jan. 31, 2005

(51) Int. Cl.
*A01H 5/00* (2006.01)

(52) U.S. Cl. ..... Plt./107
(58) Field of Classification Search ..... Plt./107, Plt./102, 137, 148, 130, 141
See application file for complete search history.

*Primary Examiner*—Howard J. Locker
(74) *Attorney, Agent, or Firm*—Klarquist Sparkman LLP

(57) ABSTRACT

Shrub rose plant suitable for cut flower production under greenhouse conditions, substantially as herein shown and described, characterized particularly by its upright growth, medium pink shallow cupped blooms having long vase life and moderate fruity fragrance.

1 Drawing Sheet

Genus and species: *Rosa hybrida.*
Variety denomination: 'AUSimmon'.

ORIGIN OF THE INVENTION

The present invention relates to a new and distinct variety of a shrub rose plant named 'AUSimmon' which was originated by me by crossing an unnamed, unpatented seedling with an unnamed, unpatented seedling.

BACKGROUND OF THE INVENTION

The primary objective of this breeding was to produce a rose plant suitable for year round cut flower production under standard greenhouse conditions having medium pink, fragrant blooms with a long vase life, produced on strong, upright stems.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Medium pink, shallow cupped blooms having long vase life.
2. Upright growth.
3. Moderate fruity fragrance.
4. Suitable for cut flower production under greenhouse conditions.

Asexual reproduction of this new variety by budding, as performed at Albrighton, England, shows that the foregoing and all other characteristics and distinctions come true to form and are established and transmitted through succeeding propagations.

COMPARISON WITH PARENTS

'AUSimmon' has large, medium pink blooms which differ from the smaller, cerise pink blooms of the seed parent and the bright crimson blooms and weaker fragrance of the pollen parent.

COMPARISON WITH SIMILAR VARIETY

'AUSwith' (U.S. Plant Pat. No. 9,010) has more petals and is pink with a tint of apricot, 'AUSimmon' is medium pink in color.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at two years of age grown in a greenhouse environment at Albrighton, England.

Blooming habit: Continuous.
Bud:
*Size.*—About 3 cm long and 1.5 cm in diameter when the petals start to unfurl.
*Form.*—The bud is long, pointed ovoid.
*Color.*—When sepals first divide, bud color is Red-Purple Group 65A. When half blown, the upper sides of the petals are Red-Purple Group 65A; and the lower sides of the petals are Red-Purple Group 58D fading to Red-Purple Group 65B on the upper third of the petal.

*Sepals*.—Color: Upper surface: Yellow-Green Group 144A. Lower surface: Green Group 141C. Length: 3 cm. Width: 0.9 cm. Shape: Subulate. Surface texture: Upper surface: Rough, with glands along central strip. Lower surface: Pubescent. There are three normally appendaged sepals. There are two unappendaged sepals with canescent edges.

*Receptacle*.—Color: Yellow-Green Group 144B. Shape: Campanulate. Size: Medium, about 1.5 cm long×1 cm wide. Surface: Smooth.

*Peduncle*.—Length: Medium, averaging about 4.7 cm. Surface: Smooth. Color: Yellow-Green Group 144A. Strength: Strong.

Bloom:

*Size*.—Large. Average open diameter is about 12 cm.

*Borne*.—In corymb shaped clusters of two to three blooms. For cut flower production buds may be nipped out to leave a single bloom.

*Flowering stems*.—Strength: Strong. Average length is about 47 cm with a diameter of 7 mm. Number: 14–16.

*Form*.—When first open: Cupped. Permanence: Outer petal edges curl slightly.

*Petalage*.—Number of petals under normal conditions: 120.

*Color*.—The upper sides of the petals are Red-Purple Group 73C. The reverse sides of the petals are Red-Purple Group 65A. The bases of the petals are Yellow Group 12C. The major color on the upper side is Red-Purple Group 73C.

*Variegations*.—None.

*Discoloration*.—The general tonality at the end of the first day: Red-Purple Group 73C. At the end of the third day: No change.

*Fragrance*.—Moderate, fruity.

Petals:

*Texture*.—Satiny, thick.

*Size*.—Width: 5.3 cm. Length: 5 cm.

*Surface*.—Smooth.

*Shape*.—Round. Margin: Entire, reflexing and slightly undulating. Apex Shape: Rounded and slightly cuspidate. Base Shape: Pointed. Form: Incurved with tips recurved.

*Arrangement*.—Irregular.

*Petaloids*.—Number: 4. Color: Red Group 48A.

*Persistence*.—Petals hang on and dry.

*Lastingness*.—On the plant: Long (about 6–8 days). As a cut flower: Long (about 6–8 days).

Reproductive parts:

*Stamens*.—Number: 80. Length: 7 mm. Anthers: Length: 3 mm. Color: Yellow-Orange Group 22A. Arrangement: Mixed with petaloids. Filaments: Color: Yellow-Orange Group 17A. Length: 4 mm. Pollen: Color: Yellow-Orange Group 22A.

*Pistils*.—Number: 55. Length: 7 mm. Styles: Color: Green-Yellow Group 1C on lower half with Red Group 53D on top half. Length: 5 mm. Stigmas: Color: Yellow Group 12B. Length: 2 mm.

*Hips*.—None observed.

PLANT

*Form*.—Shrub (grown solely for cut flower production).

*Growth*.—Vigorous, upright, bushy.

*Age at maturity*.—One and one-half years.

*Mature plant*.—Height: 1.2 m. Width: 0.6 m.

*Rootstock*.—*Rosa multiflora inermis* for the observed plants.

Foliage: Number of leaflets on normal mid-stem leaves: 5 or 7, including terminal leaflet.

*Size*.—Large. About 16.7 cm long×12.4 cm wide.

*Quantity*.—Normal. Average number leaves per flowering stem: 9.

*Color*.—New foliage: Upper side: Green Group 137D in central area of leaf and Greyed-Red Group 180A along margin. Lower side: Greyed-Red Group 180A. Old foliage: Upper side: Green Group 139A. Lower side: Green Group 137C.

Leaflets:

*Size*.—About 7 cm long×4.4 cm wide.

*Shape*.—Pointed oval.

*Base shape*.—Obtuse.

*Apex shape*.—Acuminate.

*Texture*.—Leathery, semi-glossy.

*Edge*.—Serrated.

*Serrations*.—Single.

*Petiole*.—Color: Green Group 143B.

*Petiole rachis*.—Color: Green Group 143B. Underside: With prickles.

*Stipules*.—Length: 1.2 cm, bearded.

*Auricle shape, if present*.—Linear.

*Disease resistance*.—Resistant to mildew, blackspot and rust in greenhouse maintained at about 17.5 degrees C.

*Pest resistance*.—Not tested.

*Vein color*.—Yellow-Green Group 145B.

*Venation pattern*.—Reticulate.

Wood:

*New wood*.—Color: Yellow-Green Group 144B with tint of Greyed-Orange Group 173A. Bark: Smooth.

*Old wood*.—Color: Green Group 137A. Bark: Rough.

*Internode distance*.—5 cm.

Prickles:

*Quantity*.—On main canes from base: Ordinary, 23 per 15 cm stem length. On laterals from main canes: Many, 32 per 15 cm per stem length.

*Form*.—Straight.

*Length*.—9 mm.

*Color when young*.—Yellow-Green Group 151D with Red Group 46B at base.

*Color when mature*.—Yellow-Green Group N144A and Red Group 46B on lower half.

Small prickles:

*Quantity*.—On main stalks: Ordinary. Number per stem length: 18 per 5 cm. On laterals: Many. Number per stem length: 39 per 5 cm.

*Color*.—When young: Yellow-Green Group 151D. When mature: Yellow-Green Group 151D.

Winter hardiness: Not tested.

I claim:

1. A new and distinct variety of rose plant of the shrub class suitable for cut flower production under greenhouse conditions, substantially as herein shown and described, characterized particularly by its upright growth, medium pink shallow cupped blooms having long vase life and moderate fruity fragrance.

* * * * *

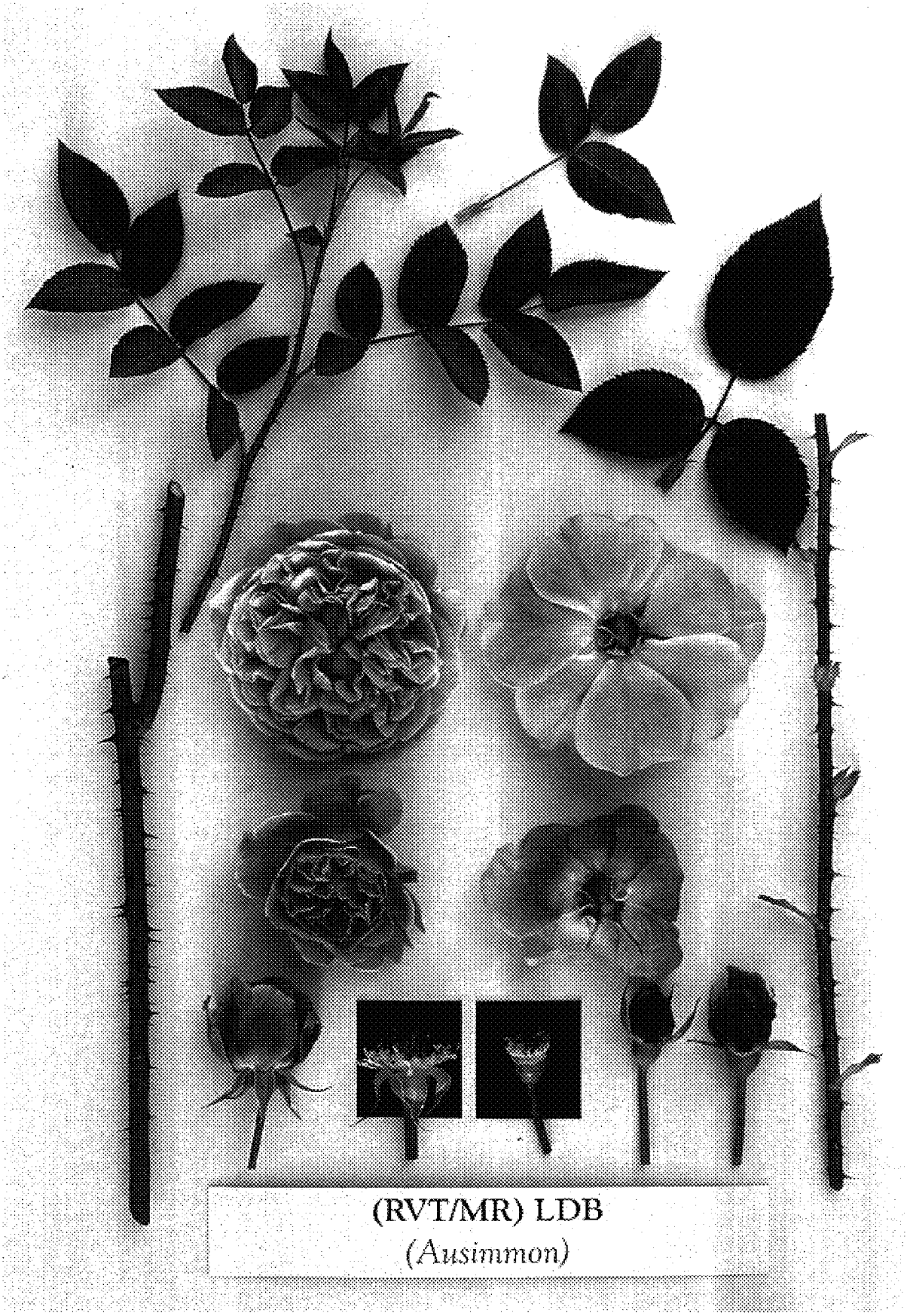
(RVT/MR) LDB
(Ausimmon)